United States Patent
Neumann et al.

[11] Patent Number: 5,072,034
[45] Date of Patent: Dec. 10, 1991

[54] PREPARATION OF 4-ALKOXY-2-HYDROXYBENZOPHENONE-5-SULFONIC ACIDS

[75] Inventors: Peter Neumann, Mannheim; Heinz Eilingsfeld, Frankenthal; Alexander Aumueller, Deidesheim, all of Fed. Rep. of Germany

[73] Assignee: BASF Aktiengesellschaft, Ludwigshafen, Fed. Rep. of Germany

[21] Appl. No.: 627,895

[22] Filed: Dec. 13, 1990

Related U.S. Application Data

[63] Continuation of Ser. No. 375,586, Jul. 5, 1989, abandoned.

Foreign Application Priority Data

Jul. 20, 1988 [DE] Fed. Rep. of Germany ....... 3824486

[51] Int. Cl.$^5$ .............................................. C07C 309/32
[52] U.S. Cl. ........................................ 562/46; 560/255; 560/14; 558/415; 558/412; 558/389
[58] Field of Search ..................... 562/46; 560/255, 14; 558/389, 412, 415

[56] References Cited

U.S. PATENT DOCUMENTS 3,468,938  9/1969  Cofrancesco et al. ................ 562/46
3,636,077  1/1972  Stauffer .................................. 562/46

Primary Examiner—Nicky Chan
Attorney, Agent, or Firm—John H. Shurtleff

[57] ABSTRACT

4-alkoxy-2-hydroxybenzophenone-5-sulfonic acids of the general formula I

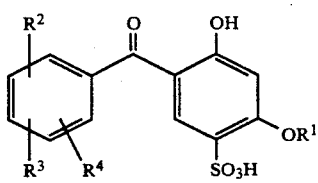

(I)

where $R^1$ is $C_1$–$C_{20}$-alkyl which is unsubstituted or substituted by halogen, cyanao, hydroxyl, $C_1$–$C_{20}$-alkoxy, $C_2$–$C_{20}$-alkoxycarbonyl, acyloxy and/or phenyl which is unsubstituted or substituted by $C_1$–$c_4$-alkyl, $C_1$–$C_4$-alkoxy and/or halogen, $R^2$ and $R^3$ independently of one another are each hydrogen, halogen, $C_1$–$C_{12}$-alkyl, $C_1$–$C_{12}$-alkoxy, $C_1$–$C_4$-haloalkyl, $C_3$–$C_8$-cycloalkyl, $C_4$–$C_{12}$-cycloalkylalkyl, cyano, hydroxyl or hydroxyethyl or are each phenoxy, $C_7$–$C_{10}$-phenalkyl or phenyl which is unsubstituted or substituted by $C_1$–$C_4$-alkyl, $C_1$–$C_4$-alkoxy and/or halogen, and $R^4$ is hydrogen or sulfo, are prepared by reacting a 4-alkoxy-2-hydroxybenzophenone of the general formula II

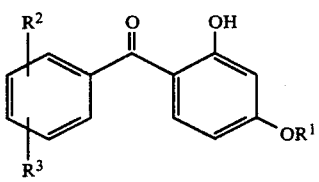

(II)

with chlorosulfonic acid at from $-20°$ to $+100°$ C., by a novel and improved process in which the reaction is carried out in an aliphatic, cycloaliphatic and/or aromatic carboxylate as solvent.

6 Claims, No Drawings

PREPARATION OF 4-ALKOXY-2-HYDROXYBENZOPHENONE-5-SULFONIC ACIDS

This application is a continuation of application Ser. No. 375,586, filed July 5, 1989, now abandoned.

The present invention relates to a novel and improved process for the preparation of 4-alkoxy-2-hydroxybenzophenone-5-sulfonic acids of the general formula I

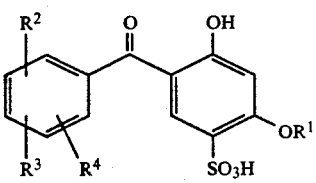

(I)

where $R^1$ is $C_1-C_{20}$-alkyl which is unsubstituted or substituted by halogen, cyano, hydroxyl, $C_1-C_{20}$-alkoxy, $C_2-C_{20}$-alkoxycarbonyl, acyloxy and/or phenyl which is unsubstituted or substituted by $C_1-C_4$-alkyl, $C_1-C_4$-alkoxy and/or halogen, $R^2$ and $R^3$ independently of one another are each hydrogen, halogen, $C_1-C_{12}$-alkyl, $C_1-C_{12}$-alkoxy, $C_1-C_4$-haloalkyl, $C_3-C_8$-cycloalkyl, $C_4-C_{12}$-cycloalkylalkyl, cyano, hydroxyl or hydroxyethyl or are each phenoxy, $C_7-C_{10}$-phenalkyl or phenyl which is unsubstituted or substituted by $C_1-C_4$-alkyl, $C_1-C_4$-alkoxy and/or halogen, and $R^4$ is hydrogen or sulfo, by reacting a 4-alkoxy-2-hydroxybenzophenone of the general formula II

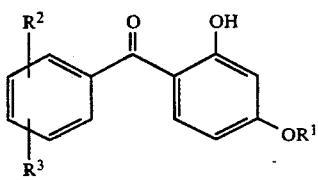

(II)

with chlorosulfonic acid at from $-20°$ to $+100°$ C., wherein the reaction is carried out in an aliphatic, cycloaliphatic and/or aromatic carboxylate as solvent.

U.S. Pat. No. 3,468,938 and U.S. Pat. No. 3,636,077 disclose that 4-alkoxy-2-hydroxybenzophenones can be prepared by reaction with chlorosulfonic acid in a chlorohydrocarbon. However, this process has a number of disadvantages, for example the toxicity of the stated solvents, so that such reactions have to be carried out in closed apparatuses, entailing expensive cleaning of the waste air and of the wastewater.

It is an object of the present invention to provide a novel and improved process for obtaining 4-alkoxy-2-hydroxybenzophenone-5-sulfonic acids and to overcome the disadvantages of the known processes.

We have found that this object is achieved by a novel and improved process for the preparation of 4-alkoxy-2-hydroxybenzophenone-5-sulfonic acids by reacting a 4-alkoxy-2-hydroxybenzophenone with chlorosulfonic acid, wherein the reaction is carried out in an aliphatic, cycloaliphatic and/or aromatic carboxylate solvent.

The 4-alkoxy-2-hydroxybenzophenone-5-sulfonic acids are obtainable by the following method:

A 4-alkoxy-2-hydroxybenzophenone is reacted with chlorosulfonic acid at from $-20°$ to $100°$ C. using an aliphatic, cycloaliphatic and/or aromatic carboxylate, in accordance with the following equation:

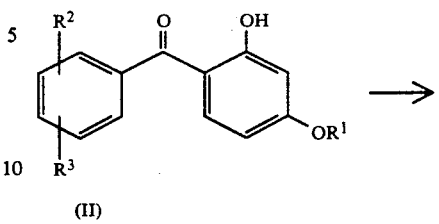

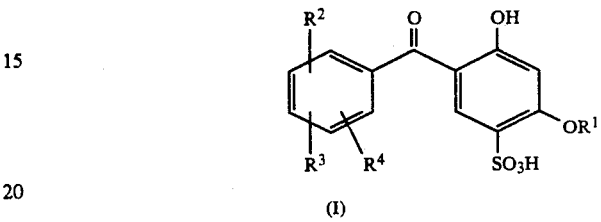

The process can be carried out continuously or batchwise.

The 4-alkoxy-2-hydroxybenzophenone II are known and can be prepared in a conventional manner, for example by Friedel-Krafts acylation of resorcinol with a carbonyl chloride of the formula III

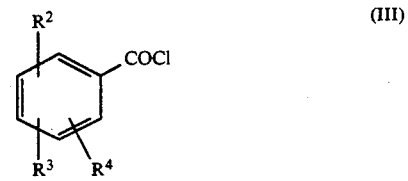

where $R^4$ is hydrogen, followed by alkylation of the hydroxyl function by a conventional method (eg. German Patent 1,917,409). Tri- and tetrahydroxybenzophenones and their ethers are obtained by the processes of U.S. Pat. No. 2,789,140, U.S. Pat. No. 2,686,812, U.S. Pat. No. 2,773,903 and U.S. Pat. No. 3,073,866.

The reaction can be carried out at from $-20°$ to $100°$ C. and under from 0.01 to 50 bar, preferably from $0°$ to $+40°$ C. and under from 0.1 to 2 bar, particularly preferably under atmospheric pressure (about 1 bar).

Suitable solvents are all carboxylates which are liquid at from $-20°$ to $+100°$ C., such as aliphatic, cycloaliphatic or aromatic mono- or polycarboxylates of aliphatic mono- or polyalcohols. They are virtually inert under the reaction conditions and can be recovered in the working up procedure in a simple manner, for example by distillation, and reused.

Instead of the pure, carboxylates, it is also possible to use mixtures, for example mixtures with industrial isooctyl alcohol, industrial isononyl alcohol, industrial isodecyl alcohol, industrial tridecyl alcohol or industrial isooctadecyl alcohol as the alcohol component. $C_1-C_4$-alkyl esters of acetic acid, propionic acid, benzoic acid or phthalic acid are preferred, in particular ethyl and butyl acetate, methyl and ethyl benzoate and methyl, ethyl and butyl phthalate.

Examples of the esters of carboxylic acids such as acetic acid, propionic acid, 2-methylbutyric acid, butyric acid, isobutyric acid, valeric acid, isovaleric acid, pivalic acid, caproic acid, enanthic acid, 2-ethylhexanoic acid, caprylic acid, capric acid, lauric acid, myristic acid, palmitic acid, stearic acid, arachic acid, behenic acid, lignoceric acid, cyclohexanecarboxylic acid, oxalic acid, malonic acid, succinic acid, glutaric acid, adipic acid, suberic acid, sebacic acid, benzoic acid, 2-, 3- or 4-fluorobenzoic acid, 2-, 3- or 4-chlorobenzoic acid, 2-, 3- or 4-methylbenzoic acid, phthalic acid, isophthalic acid and terephthalic acid with alcohols such as methanol, ethanol, 1-butanol, isobutanol, sec-butanol, tert-butanol, 1-pentanol, 2-methyl-1-butanol, 3-methyl-1-butanol, 2-methyl-2-butanol, 2,2-dimethyl-1-propanol, 1-hexanol, 2-ethyl-1-butanol, 2-hexanol, 1-heptanol, 1-octanol, 2-ethyl-1-hexanol, 3,3-dimethyl-1-hexanol, 3,5-dimethyl-1-hexanol, 4,5-dimethyl- 1-1-hexanol, 1-nonanol, 3,5,5-trimethyl-1-hexanol, 1-decanol, 3,5-dimethyoctanol, 1-undecanol, 1-dodecanol, 1-tridecanol, 1-tetradecanol, 1-pentadecanol, 1-hexadecanol, 1-heptadecanol, 1-octadecanol, 1-nonadecanol, 1-eicosanol, 1-heneicosanol, 1-docosanol, 1-tricosanol, 1-tetracosanol, 1-pentacosanol, 1-hexacosanol, 1-heptacosanol, 1-octacosanol, 1-nonacosanol, 1-triacontanol, cyclohexanol, ethylene glycol, glycerol, propylene glycol, 1,2-butanediol, 1,4-butanediol, 2,3-butanediol, 1,2,4-butanetriol, 1,2-pentanediol, 2,2-dimethyl-1,3-propanediol, 1,5-pentanediol, 1,6-hexanediol, pentaerythritol, trimethylolethane and trimethylolpropane.

Specific examples of esters are the following: methyl acetate, ethyl acetate, propyl acetate, isopropyl acetate, butyl acetate, isobutyl acetate, 2-ethylhexyl acetate, ethylene glycol acetate, glyceryl triacetate, glyceryl tripropionate, glyceryl tripalmitate, isobutyl isobutyrate, bis-(2-ethylhexyl) adipate, butyl glycolate, dimethyl phthalate, diethyl phthalate, dibutylphthalate, bis-(2-ethylhexyl) phthalate, bis-(2-ethylhexyl) terephthalate and bis-(2-ethylhexyl) trimellitate.

The amount of the solvent can vary within wide limits, for example from 500 to 5,000 ml, preferably from 500 to 2,500 ml, particularly preferably from 500 to 2,000 ml, per mole of 4-alkoxy-2-hydroxybenzophenone II.

In the sulfonation according to the invention, a sulfo group is, as a rule, introduced into the 4-alkoxy-2-hydroxy nucleus of the starting compound. If the reactivity of the second nucleus has been increased by appropriate substitution with electron donor groups, such as hydroxyl or alkoxy, it is also possible to introduce two sulfo radicals; for example, the reaction of 2,2'-dihydroxy-4,4'-dimethoxybenzophenone with 2 moles of sulfonating reagent gives the 2,2'-dihydroxy-4,4'-dimethoxy-5,5'-disulfonic acid.

In the monosulfonation, educt (II) and the sulfonating agent chlorosulfonic acid are reacted in a molar ratio of from 0.01:1 to 10:1, preferably from 0.1:1 to 1.2:1, particularly preferably about 1:1; a small excess (from 1 to 20 mol %) of the sulfonating agent is advantageous in order to achieve complete conversion.

Working up of the crude reaction mixture and isolation of the sulfonic acid (I) can be carried out in a conventional manner, for example by filtering off under suction the reaction product precipitated after the end of the reaction, if necessary on cooling, or by evaporating down the reaction mixture under atmospheric or reduced pressure. In another working up procedure, after the reaction is complete, the reaction mixture is run into initially taken water or water is added to the reaction mixture; in this case, prior cooling of the reaction mixture can be dispensed with. The end products (II) can then be isolated from the aqueous solution by spray drying, as described in U.S. Pat. No. 3,468,938, or can be precipitated as sparingly water-soluble alkali metal or alkaline earth metal salts or ammonium salts or, for example, isolated by extraction with amines in the form of ammonium salts.

The substituents in formulae I and II have the following meanings:

$R^1$ is straight-chain or branched $C_1$–$C_{20}$-alkyl, preferably straight-chain or branched $C_1$–$C_{18}$-alkyl, such as methyl, ethyl, n-propyl, isopropyl, n-butyl, isobutyl, sec-butyl, tert-butyl, n-pentyl, isopentyl, sec-pentyl, tert-pentyl, neopentyl, 1,2-dimethylpropyl, n-hexyl, isohexyl, sec-hexyl, n-heptyl, isoheptyl, n-octyl, isooctyl, 1,1,3,3-tetramethylbutyl, nonyl, isononyl, n-decyl, isodecyl, n-undecyl, isoundecyl, n-dodecyl, isododecyl, n-tridecyl, n-tetradecyl, n-pentadecyl, n-hexadecyl, n-heptadecyl or n-octadecyl, straight-chain or branched $C_1$–$C_{20}$-haloalkyl, preferably straight-chain or branched $C_1$–$C_8$-fluoro- or chloroalkyl, particularly preferably straight-chain or branched $C_1$–$C_4$-fluoro- and or chloroalkyl, such as 2-chloroethyl or 2,2,2-trifluoroethyl, straight-chain or branched $C_1$–$C_{20}$-cyanoalkyl, preferably straight-chain or branched $C_1$–$C_8$-cyanoalkyl, particularly preferably straight-chain or branched $C_1$–$C_4$-cyanoalkyl, such as cyanomethyl, 1-cyanoethyl, 2-cyanoethyl or 4-cyanobutyl, straight-chain or branched $C_2$–$C_{20}$-hydroxyalkyl, preferably straight-chain or branched $C_2$–$C_8$-hydroxyalkyl, particularly preferably straight-chain or branched $C_2$–$C_4$-hydroxyalkyl, such as 2-hydroxyethyl, 3-hydroxypropyl or 4-hydroxybutyl, straight-chain or branched $C_2$–$C_{40}$-alkoxyalkyl, preferably $C_2$–$C_{20}$-alkoxyalkyl, particularly preferably $C_2$–$C_8$-alkoxyalkyl, such as methoxymethyl, 1-methoxyethyl, 2-methoxyethyl or ethoxymethyl, straight-chain or branched $C_1$–$C_{20}$-alkyl substituted by $C_2$–$C_{20}$-alkoxycarbonyl, preferably straight-chain or branched $C_1$–$C_8$-alkyl substituted by $C_2$–$C_8$-alkoxycarbonyl, particularly preferably straight-chain or branched $C_1$–$C_4$-alkyl substituted by $C_2$–$C_5$-alkoxycarbonyl, such as methoxycarbonylmethyl, ethoxycarbonylmethyl, n-propoxycarbonylmethyl, butoxycarbonylmethyl, 2-methoxycarbonylethyl, 2-ethoxycarbonylethyl, 2-n-propoxycarbonylethyl, 2-n-butoxy-carbonylethyl, 3-methoxycarbonylpropyl, 3-ethoxycarbonylpropyl, 3-n-propoxycarbonylpropyl, 3-butoxycarbonylpropyl, 4-methoxycarbonylbutyl, 4-ethoxycarbonylbutyl, 4-n-propoxycarbonylbutyl or 4-n-butoxycarbonylbutyl, straight-chain or branched $C_2$–$C_{20}$-alkyl which is substituted by $C_1$–$C_{20}$-acyloxy, preferably straight-chain or branched $C_2$–$C_8$-alkyl which is substituted by acyloxy, particularly preferably straight-chain or branched $C_2$–$C_4$-alkyl which is substituted by $C_1$–$C_4$-acyloxy, such as 2-acetyloxyethyl, 2-propanoyloxyethyl, 2-butanoyloxyethyl, 3-acetyloxypropyl, 3-propanoyloxypropyl, 3-butanoyloxypropyl, 4-acetyloxybutyl, 4-propanoyloxybutyl or 4-butanoyloxybutyl, straight-chain or branched $C_7$–$C_{26}$-phenalkyl, preferably straight-chain or branched $C_7$–$C_{14}$-phenalkyl, particularly preferably straight-chain or branched $C_7$–$C_{10}$-phenalkyl, such as benzyl, 1-phenethyl, 2-phenethyl, 3-phenpropyl and 4-phenbutyl, straight-chain or branched $C_7$–$C_{26}$-phenalkyl, which is monosubstituted to trisubstituted in the phenyl moiety by $C_1$–$C_4$-alkyl, preferably straight-chain or branched $C_7$–$C_{14}$-phenalkyl which is monosubstituted to trisubstituted in the phenyl moiety by $C_1$-$C_4$-alkyl, particularly preferably straight-chain or branched $C_7$-$C_{10}$-phenalkyl which is monosubstituted in alkyl, such as 2-methylbenzyl or 4-methylbenzyl, straight-chain or branched $C_7$-$C_{26}$-phenalkyl which is monosubstituted to trisubstituted in the phenyl moiety by $C_1$-$C_4$-alkoxy, particularly preferably $C_7$-$C_{14}$-phenalkyl which is monosubstituted to trisubstituted in the phenyl moiety by $C_1$-$C_4$-alkoxy, particularly preferably straight-chained or branched $C_7$-$C_{10}$-phenalkyl which is monosubstituted in the phenyl moiety by $C_1$-$C_4$-alkoxy, such as 2-methoxybenzyl, 4-methoxybenzyl, 2-ethoxybenzyl or 4-ethoxybenzyl, straight-chain or branched $C_7$-$C_{26}$-phenalkyl which is monosubstituted to trisubstituted in the phenyl moiety by halogen, preferably straight-chain or branched $C_7$-$C_{14}$-phenalkyl, which is monosubstituted to trisubstituted in the phenyl moiety by fluorine and/or chlorine, particularly preferably straight-chain or branched $C_7$-$C_{10}$-phenalky which is monosubstituted in the phenyl moiety by fluorine or chlorine, such as 2-fluorobenzyl, 4-fluorobenzyl, 2-chlorobenzyl or 4-chlorobenzyl, straight-chain or branched $C_7$-$C_{26}$-phenalkyl which is disubstituted or trisubstituted in the phenyl moiety by $C_1$-$C_4$-alkyl and $C_1$-$C_4$-alkoxy, preferably straight-chain or branched $C_7$-$C_{10}$-phenalkyl which is disubstituted or trisubstituted in the phenyl moiety by $C_1$-$C_4$-alkyl and $C_1$-$C_4$-alkoxy, such as 3-methyl-4-methoxybenzyl or 3,5-di-methyl-4-methoxybenzyl, straight-chain or branched $C_7$-$C_{26}$-phenalkyl which is disubstituted or trisubstituted in the phenyl moiety by $C_1$-$C_4$-alkyl and halogen, preferably straight-chain or branched $C_7$-$C_{10}$-phenalkyl which is disubstituted or trisubstituted in the phenyl moiety by $C_1$-$C_4$-alkyl and halogen, such as 3-chloro-4-methylbenzyl, straight-chain or branched $C_7$-$C_{26}$-phenalkyl which is disubstituted or trisubstituted in the phenyl moiety by $C_1$-$C_4$-alkoxy and halogen, preferably straight-chain or branched $C_7$-$C_{10}$-phenalkyl which is disubstituted to trisubstituted in the phenyl moiety by $C_1$-$C_4$-alkoxy and halogen, such as 3-chloro-4-methoxybenzyl, straight-chain or branched $C_7$-$C_{26}$-phenalkyl which is substituted in the phenyl moiety by $C_1$-$C_4$-alkyl, $C_1$-$C_4$-alkoxy and halogen, preferably straight-chain or branched $C_7$-$C_{10}$-phenalkyl which is substituted in the phenyl moiety by $C_1$-$C_4$-alkyl, $C_1$-$C_4$-alkoxy and halogen, such as 2-chloro-3-methyl-4-methoxybenzyl, and $R^2$ and $R^3$ independently of one another are each hydrogen, halogen, such as fluorine, chlorine, bromine or iodine, preferably fluorine or chlorine, straight-chain or branched $C_1$-$C_{12}$-alkyl, such as methyl, ethyl, n-propyl, isopropyl, n-butyl, isobutyl, sec-butyl, tert-butyl, n-pentyl, isopentyl, sec-pentyl, tert-pentyl, neopentyl, 1,2-dimethylpropyl, n-hexyl, isohexyl, sechexyl, n-heptyl, isoheptyl, n-octyl, isooctyl, n-nonyl, isononyl, n-decyl, isodecyl, n-undecyl, isoundecyl, n-dodecyl or isododecyl, straight-chain or branched $C_1$-$C_{12}$-alkoxy, such as methoxy, ethoxy, n-propoxy, isopropoxy, n-butoxy, isobutoxy, sec-butoxy, tert-butoxy, n-pentyloxy, isopentyloxy, sec-pentyloxy, tert-pentyloxy, neopentyloxy, 1,2-dimethylpropoxy, n-hexyloxy, isohexyloxy, sechexyloxy, n-heptyloxy, isoheptyloxy, n-octyloxy, isooctyloxy, 1,1,3,3-tetramethylbutoxy, n-nonyloxy, isononyloxy, n-decyloxy, isodecyloxy, n-undecyloxy, isoundecyloxy, n-dodecyloxy or isododecyloxy, straight-chain or branched $C_1$-$C_4$-haloalkyl, such as 1,2-dibromo-2,2,-dimethylethyl, preferably $C_1$ or $C_2$-fluoro- or chloroalkyl, such as fluoromethyl, difluoromethyl, trifluoromethyl, chloromethyl, chlorofluoromethyl, dichlorofluoromethyl, chlorodifluoromethyl, 2,2,2-trifluoroethyl or 2,2,2-trichloroethyl, $C_3$-$C_8$-cycloalkyl, such as cyclopropyl, cyclobutyl, cyclopentyl, cyclohexyl, cycloheptyl or cyclooctyl, preferably cyclohexyl, $C_4$-$C_{12}$-cycloalkylalkyl, such as cyclopropylmethyl, cyclopentylmethyl, cyclohexylmethyl, cycloheptylmethyl, cyclooctylmethyl or 2-cyclohexylethyl, cyano, hydroxyl, hydroxyethyl, phenyl, phenoxy, $C_7$-$C_{10}$-phenalkyl, such as benzyl, 1-phenethyl, 2-phenethyl, 2-phenpropyl, 3-phenpropyl or 4-phenbutyl, phenyl which is monosubstituted or disubstituted, preferably monosubstituted, by $C_1$-$C_4$-alkyl, such as 2-methylphenyl, 3-methylphenyl, 4-methylphenyl, 2-ethylphenyl, 3-ethylphenyl, 4-ethylphenyl, 2-n-propylphenyl, 3-n-propylphenyl, 4-n-propylphenyl, 3-isopropylphenyl, 4-isopropylphenyl, 2-n-butylphenyl, 3-n-butylphenyl, 4-n-butylphenyl, 3-isobutylphenyl, 4-isobutylphenyl, 3-sec-butylphenyl, 4-sec-butylphenyl, 3-tert-butylphenyl, 4-tert-butylphenyl, 2,3-dimethylphenyl, 2,4-dimethylphenyl, 2,5-dimethylphenyl, 3,4-dimethylphenyl, 3,5-dimethylphenyl, 2,6-dimethylphenyl, 3,6-dimethylphenyl, 2,4-diethylphenyl, 2,4-diisopropylphenyl, 3,5-di-tert-butylphenyl or 2,6-di-tert-butylphenyl, phenyl which is monosubstituted or disubstituted, preferably monosubstituted by $C_1$-$C_4$-alkoxy, such as 2-methoxyphenyl, 3-methoxyphenyl, 4-methoxyphenyl, 2-ethoxyphenyl, 3-ethoxyphenyl, 4-ethoxyphenyl, 2-n-propoxyphenyl, 3-n-propoxyphenyl, 4-n-propoxyphenyl, 3-isopropoxyphenyl, 4-isopropoxyphenyl, 2-n-butoxyphenyl, 3-n-butoxyphenyl, 4-n-butoxyphenyl, 2-sec-butoxyphenyl, 4-sec-butoxyphenyl, 2-tert-butoxyphenyl, 4-n-hexoxyphenyl, 2,3-dimethoxyphenyl, 2,4-dimethoxyphenyl, 3,4-dimethoxyphenyl, 2,5-dimethoxyphenyl, 3,5-dimethoxyphenyl, 2,6-dimethoxyphenyl or 3,4-diethoxyphenyl, phenyl which is monosubstituted or disubstituted by halogen, preferably phenyl which is monosubstituted by fluorine or chlorine, such as 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2,3-difluorophenyl, 2,3-dichlorophenyl, 2,4-difluorophenyl, 2,4-dichlorophenyl, 2-chloro-4-fluorophenyl, 4-chloro-2-fluorophenyl, 2,5-difluorophenyl, 2,5-dichlorophenyl, 3,4-difluorophenyl, 3,4-dichlorophenyl, 3,5-difluorophenyl, 3,5-dichlorophenyl, 3-chloro-5-fluorophenyl, 5-chloro-3-fluorophenyl, 2,6-difluorophenyl, 2,6-dichlorophenyl, 2-chloro-6-fluorophenyl or 6-chloro-2-fluorophenyl, phenyl which is substituted by $C_1$-$C_4$-alkyl and $C_1$-$C_4$-alkoxy, such as 2-methyl-4-methoxyphenyl, phenyl which is substituted by $C_1$-$C_4$-alkyl and halogen, such as 2-methyl-4-chlorophenyl or 3-methyl-4-fluorophenyl, phenyl which is substituted by $C_1$-$C_4$-alkoxy and halogen, such as 3-chloro-4-methoxyphenyl, phenoxy which is monosubstituted or disubstituted by $C_1$-$C_4$-alkyl, such as 2-methylphenoxy, 3-methylphenoxy, 4-methylphenoxy, 2-ethylphenoxy, 3-ethylphenoxy, 4-ethylphenoxy, 2-n-propylphenoxy, 3-n-propylphenoxy, 4-n-propylphenoxy, 3-isopropylphenoxy, 4-isopropylphenoxy, 2-n-butylphenoxy, 3-n- butylphenoxy, 4-n-butylphenoxy, 2-sec-butylphenoxy, 4-sec-butylphenoxy, 2-tert-butylphenoxy, 4-n-hexylphenoxy, 2,3-dimethylphenoxy, 2,4-dimethylphenoxy, 3,4-dimethylphenoxy, 2,5-dimethylphenoxy, 3,5-dimethylphenoxy, 2,6-dimethylphenoxy or 3,4-diethylphenoxy, phenoxy which is monosubstituted or disubstituted by $C_1$–$C_4$-alkoxy, such as 2-methoxyphenoxy, 3-methoxyphenoxy, ethoxyphenoxy, 2-n-propoxyphenoxy, 3-n-propoxyphenoxy, 4-n-propoxyphenoxy, 3-isopropoxyphenoxy, 4-isopropoxyphenoxy, 2-n-butoxyphenoxy, 3-n-butoxyphenoxy, 4-n-butoxyphenoxy, 3-isobutoxyphenoxy, 4-isobutoxyphenoxy, 3-sec-butoxyphenoxy, 4-sec-butoxyphenoxy, 3-tert-butoxyphenoxy, 4-tert-butoxyphenoxy, 2,3-dimethoxyphenoxy, 2,4-dimethoxyphenoxy, 2,5-dimethoxyphenoxy, 3,4-dimethoxyphenoxy, 3,5-dimethoxyphenoxy, 2,6-dimethoxyphenoxy, 3,6-dimethoxyphenoxy, 2,4-diethoxyphenoxy, 2,4-diisopropoxyphenoxy, 3,5-di-tert-butoxyphenoxy or 2,6-di-tert-butoxyphenoxy, phenoxy which is monosubstituted or disubstituted by halogen, preferably phenoxy which is monosubstituted by fluorine and/or chlorine, such as 2-fluorophenoxy, 2-chlorophenoxy, 3-fluorophenoxy, 3-chlorophenoxy, 4-fluorophenoxy, 4-chlorophenoxy, 2,3-difluorophenoxy, 2,3-dichlorophenoxy, 2,4-difluorophenoxy, 2,4-dichlorophenoxy, 2-chloro-4-fluorophenoxy, 4-chloro-2-fluorophenoxy, 2,5-difluorophenoxy, 2,5-dichlorophenoxy, 3,4-difluorophenoxy, 3,4-dichlorophenoxy, 3,5-difluorophenoxy, 3,5-dichlorophenoxy, 3-chloro-5-fluorophenoxy, 5-chloro-3-fluorophenoxy, 2,6-difluorophenoxy, 2,6-dichlorophenoxy, 2-chloro-6-fluorophenoxy or 6-chloro-2-fluorophenoxy, phenoxy which is substituted by $C_1$–$C_4$-alkyl and $C_1$–$C_4$-alkoxy, such as 2-methyl-4-methoxyphenoxy, phenoxy which is substituted by $C_1$–$C_4$-alkyl and halogen, such as 2-methyl-4-chlorophenoxy and 3-methyl-4-fluorophenoxy, phenoxy which is substituted by $C_1$–$C_4$-alkoxy and halogen, such as 3-chloro-4-methoxyphenoxy, $C_7$–$C_{10}$-phenalkyl which is monosubstituted or disubstituted by $C_1$–$C_4$-alkyl, such as 4-methylbenzyl or 3,4-dimethylbenzyl, $C_7$–$C_{10}$-phenalkyl which is monosubstituted or disubstituted by $C_1$–$C_4$-alkoxy, such as 4-methoxybenzyl or 3,4-dimethoxybenzyl, $C_7$–$C_{10}$-phenalkyl which is monosubstituted or disubstituted by halogen, preferably $C_7$–$C_{10}$-phenalkyl which is monosubstituted or disubstituted by fluorine or chlorine, such as 4-fluorobenzyl or 4-chlorobenzyl, and $R^4$ is hydrogen or
sulfo.

With regard to the use of the 4-alkoxy-2-hydroxybenzophenone-5-sulfonic acids I as light stabilizers, particularly preferred radicals are those in which $R^1$ is $C_1$–$C_{18}$-alkyl, $R^2$ is in the ortho-position to the ketonic carbonyl group and is hydrogen or hydroxyl and $R^4$ is hydrogen. Other important compounds I are those in which $R^1$ is $C_1$–$C_{18}$-alkyl, $R^2$ and/or $R^3$ are each hydrogen or $R^2$ is an ortho-hydroxyl group and $R^3$ is a para-alkoxy group, and $R^4$ is hydrogen.

In general, the 4-alkoxy-2-hydroxybenzophenone-5-sulfonic acids I are obtained in sufficient purity; however, a further purification step can readily be combined with the working up, by, for example, adding active carbon to the aqueous solution described above, filtering the solution and isolating the compounds I from the filtrate in the manner described above. Subsequent purification, for example by reprecipitation from aqueous solution or stirring or washing with a solvent, can also be carried out.

Depending on the working up procedure, the hygroscopic 4-alkoxy-2-hydroxybenzophenone-5-sulfonic acids I may have a water content of from 0.01 to 20, preferably from 0.5 to 15%, by weight. The water content does not present problems during use.

The 4-alkoxy-2-hydroxybenzophenone-5-sulfonic acids I are suitable, for example, as light stabilizers, for example in cosmetic preparations.

Regarding their use as light stabilizers, particularly suitable compounds I are the following:
2-hydroxy-4-methoxybenzophenone-5-sulfonic acid,
2-hydroxy-4-ethoxybenzophenone-5-sulfonic acid,
2-hydroxy-4-n-propoxybenzophenone-5-sulfonic acid,
2-hydroxy-4-isopropoxybenzophenone-5-sulfonic acid,
2-hydroxy-4-n-butoxybenzophenone-5-sulfonic acid,
2-hydroxy-4-isobutoxybenzophenone-5-sulfonic acid,
2-hydroxy-4-sec-butoxybenzophenone-5-sulfonic acid,
2-hydroxy-4-n-pentyloxybenzophenone-5-sulfonic acid,
2-hydroxy-4-n-hexyloxybenzophenone-5-sulfonic acid,
2-hydroxy-4-isohexyloxybenzophenone-5-sulfonic acid,
2-hydroxy-4-n-heptyloxybenzophenone-5-sulfonic acid,
2-hydroxy-4-isoheptyloxybenzophenone-5-sulfonic acid,
2-hydroxy-4-n-octyloxybenzophenone-5-sulfonic acid,
2-hydroxy-4-(3,4-dimethyl-1-hexyloxy)-benzophenone-5-sulfonic acid,
2-hydroxy-4-(3,5-dimethyl-1-hexyloxy)-benzophenone-5-sulfonic acid,
2-hydroxy-4-(4,5-dimethyl-1-hexyloxy)-benzophenone-5-sulfonic acid,
2-hydroxy-4-(3-methyl-1-heptyloxy)-benzophenone-5-sulfonic acid,
2-hydroxy-4-n-nonyloxybenzophenone-5-sulfonic acid,
2-hydroxy-n-decyloxybenzophenone-5-sulfonic acid,
2-hydroxy-4-n-undecyloxybenzophenone-5-sulfonic acid,
2-hydroxy-4-n-dodecyloxybenzophenone-5-sulfonic acid,
2-hydroxy-4-n-hexadecyloxybenzophenone-5-sulfonic acid,
2-hydroxy-4-n-octadecyloxybenzophenone-5-sulfonic acid,
2-hydroxy-4-(2-acetoxyethoxy)-benzophenone-5-sulfonic acid,
2-hydroxy-4-(2-phenbenzoyloxyethoxy)-benzophenone-5-sulfonic acid,
2-hydroxy-4-phenylmethyleneoxybenzophenone-5-sulfonic acid,
2-hydroxy-4-(2-phenylethyleneoxy)-benzophenone-5-sulfonic acid,
2,2'-dihydroxy-4,4'-dimethoxybenzophenone-5-sulfonic acid,
2,2'-dihydroxy-4,4'-dimethoxybenzophenone-5,5'-sulfonic acid,
2,2'-dihydroxy-4-methoxybenzophenone-5-sulfonic acid,
2-hydroxy-4'-fluoro-4-methoxybenzophenone-5-sulfonic acid,
2-hydroxy-4-methoxy-4'-methylbenzophenone-5-sulfonic acid,
2-hydroxy-4-methoxy-4'-phenoxybenzophenone-5-sulfonic acid,
2-hydroxy-4-methoxy-4'-chlorobenzophenone-5-sulfonic acid,
2-hydroxy-4-methoxycarbonylmethyleneoxybenzophenone-5-sulfonic acid and 2-hydroxy-4-ethoxycarbonylmethyleneoxybenzophenone-5-sulfonic acid.

EXAMPLES

Preparation of
2-hydroxy-4-methoxybenzophenone-5-sulfonic acid
(Examples 1 to 3)

EXAMPLE 1

22.8 g of 2-hydroxy-4-methoxybenzophenone were introduced into 60 ml of ethyl acetate, 31 g of chlorosulfonic acid were added dropwise in the course of 30 minutes while cooling (internal temperature about 0°–5° C.), and the mixture was stirred overnight at room temperature (18°–25° C.). Thereafter, the mixture was cooled to 10° C. and the product was filtered off under suction, washed with 10 ml of ethyl acetate and dried at 30° C. under reduced pressure. 26 g of 2-hydroxy-4-methoxybenzophenone-5-sulfonic acid of melting point 193°–195° C. and having a water content of 3.7% by weight were obtained.

EXAMPLE 2

22.8 g (0.1 mole) of 2-hydroxy-4-methoxybenzophenone, dissolved in a mixture of 43 ml of filtrate from Example 1 and 17 ml of ethyl acetate, were reacted at room temperature similarly to Example 1, 27 g of 2-hydroxy-4-benzophenone-5-sulfonic acid of melting point 196°–198° C. being obtained after drying at 30°–40° C. under reduced pressure (water content 2.5% by weight).

EXAMPLE 3

11.4 g of 2-hydroxy-4-methoxybenzophenone were dissolved in 30 ml of ethyl benzoate at room temperature, a pinch of 2-hydroxy-4-methoxybenzophenone-5-sulfonic acid was added and 3.5 ml of chlorosulfonic acid were added dropwise in the course of 30 minutes with external cooling (about . . . °C.). Crystallization began after about 20 minutes. Stirring was carried out for a further 4 hours at room temperature, the mixture was cooled to 10° C. and the product was filtered off under suction, washed twice with a little methyl acetate and dried at 30° C. under reduced pressure. 13.5 g of 2-hydroxy-4-methoxybenzophenone-5-sulfonic acid of melting point 188°–190° C. were obtained (water content <0.5% by weight).

EXAMPLE 4

Preparation of
2,2'-dihydroxy-4,4'-dimethoxybenzophenone-5sulfonic acid 3.5 ml (0.05 mole) of chlorosulfonic acid were added dropwise to a suspension of 13.7 g (0.05 mole) of 2,2'-dihydroxy-4,4'-dimethoxybenzophenone in 50 ml of ethyl benzoate at 20° C. Thereafter, stirring was carried out for 4 hours at 20° C., and the precipitate was filtered off under suction, washed with twice 10 ml of ethyl acetate and stirred with 30 ml of diethyl ether. Drying under reduced pressure at 30° C. gave 9.1 g of 2,2'-dihydroxy-4,4'-dimethoxybenzophenone-5-sulfonic acid of melting point 151°–153° C. (water content 2.4% by weight).

EXAMPLE 5

11.4 g of 2-hydroxy-4-methoxybenzophenone were dissolved in 30 ml of dimethyl phthalate at 80° C., and 3.5 ml of chlorosulfonic acid were added dropwise at this temperature. Stirring was carried out for a further 4 hours at 80° C., the mixture was cooled to room temperature and 25 ml of ether were added to the solution. The precipitate was filtered off under suction, washed with ether and hexane and dried under reduced pressure at 30° C. 10 g of 2-hydroxy-4-methoxybenzophenone-5-sulfonic acid of melting point 112°–114° C. were obtained (water content 7.7%).

EXAMPLE 6

6.56 g of 2-hydroxy-4-methoxy-4'-chlorobenzophenone were dissolved in 25 ml of ethyl benzoate at room temperature, and 1.75 ml of chlorosulfonic acid were added dropwise. Stirring was carried out for 4 hours at room temperature, after which the reaction mixture was poured onto 50 ml of water, and the aqueous phase was separated off and evaporated down under reduced pressure (about 10 mbar). The residue was stirred with about 30 ml of ether, filtered off under suction, washed with ether and dried under reduced pressure at 30° C. 7.4 g of 2-hydroxy-4-methoxy-4'-chlorobenzophenone-5-sulfonic acid of melting point 123°–125° C. were obtained (water content 9.5%).

EXAMPLE 7

8 g of 2-hydroxy-4-methoxy-4'-phenoxybenzophenone were dissolved in 15 ml of ethyl benzoate at room temperature, and 1.75 ml of chlorosulfonic acid were added dropwise. Stirring was carried out for 12 hours at room temperature, after which the pasty reaction mixture was stirred with 30 ml of ether, and the residue was filtered off under suction, washed with ether and dried under reduced pressure at 30° C. 4.3 g of 2-hydroxy-4-methoxy-4'-phenoxybenzophenone-5-sulfonic acid of melting point 169°–171° C. were obtained (water content 1.2%).

EXAMPLE 8

6.45 g of 2-hydroxy-4,4'-dimethoxybenzophenone were dissolved in 25 ml of ethyl benzoate at room temperature, and 1.75 ml of chlorosulfonic acid were added dropwise. The procedure was continued similarly to Example 6, and 7.3 g of 2-hydroxy-4,4'-dimethoxybenzophenone-5-sulfonic acid of melting point 125°–127° C. were obtained (water content 10.5%).

EXAMPLE 9

3.5 ml of chlorosulfonic acid was added dropwise to a suspension of 13.7 g of 2,2'-dihydroxy-4,4'-dimethoxybenzophenone in 50 ml of ethyl benzoate. In the course of the dropwise addition, a clear solution was temporarily formed, from which a precipitate separated out in the course of stirring for 4 hours at room temperature. The mixture was cooled to 10° C., after which the precipitate was filtered off under suction and washed with twice 10 ml of cold (about 10° C.) ethyl acetate. The residue was stirred twice with 30 ml of ether in each case, filtered off under suction and dried under reduced pressure at 30° C. 7 g of 2,2'-dihydroxy-4,4'-dimethoxybenzophenone-5-sulfonic acid of melting point 160°–162° C. were obtained (water content 1.7%).

EXAMPLE 10

21.3 g of 2-hydroxy-4-n-octyloxybenzophenone were dissolved at room temperature in 30 ml of ethyl benzoate, and 3.5 ml of chlorosulfonic acid were added dropwise. The mixture was stirred for 4 hours at room temperature and then cooled to 10° C., and the precipitate was filtered off under suction and washed with 10 ml of ethyl acetate. The residue was stirred with 10 ml of hexane and dried under reduced pressure. 3.6 g of 2-hydroxy-4-n-octyloxybenzophenone-5-sulfonic acid of melting point 165°–167° C. were obtained (water content 4.4%). After 40 ml of hexane had been added to the remaining ethyl benzoate solution, a further 13 g of the sulfonic acid were obtained.

EXAMPLE 11

2.8 g of 2-hydroxy-4-methoxycarbonylmethyleneoxybenzophenone were suspended at room temperature in 10 ml of ethyl benzoate, and 0.7 ml of chlorosulfonic acid was added dropwise. The mixture was stirred for 4 hours at room temperature and the precipitate was filtered off under suction and washed twice with about 5 ml of ethyl acetate in each case. Stirring was residue with about 10 ml of ether and drying under reduced pressure at 30° C. gave 1.9 g of 2-hydroxy-4-methoxycarbonylmethyleneoxybenzophenone-5-sulfonic acid of melting point 145°–146° C. (water content 4.5%).

We claim:

1. A process for the preparation of a 4-alkoxy-2-hydroxybenzophenone-5-sulfonic acid of the formula

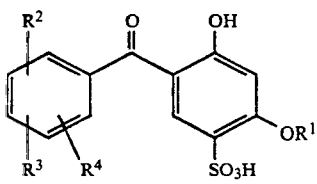

where $R^1$ is $C_1$–$C_{20}$-alkyl which is unsubstituted or substituted by halogen, cyano, hydroxyl, $C_1$–$C_{20}$-alkoxy, $C_2$–$C_{20}$-alkoxycarbonyl, acyloxy and/or phenyl which is unsubstituted or substituted by $C_1$–$C_4$-alkyl, $C_1$–$C_4$-alkoxy and/or halogen, $R^2$ and $R^3$ independently of one another are each hydrogen, halogen, $C_1$–$C_{12}$-alkyl, $C_1$–$C_{12}$-alkoxy, $C_1$–$C_4$-haloalkyl, $C_3$–$C_8$-cycloalkyl, $C_4$–$C_{12}$-cycloalkylalkyl, cyano, hydroxyl or hydroxyethyl or are each phenoxy, $C_7$–$C_{10}$-phenalkyl or phenyl, which is unsubstituted or substituted by $C_1$–$C_4$-alkyl, $C_1$–$C_4$-alkoxy and/or halogen, and $R^4$ is hydrogen or sulfo, which comprises:

reacting a 4-alkoxy-2-hydroxybenzophenone of the formula

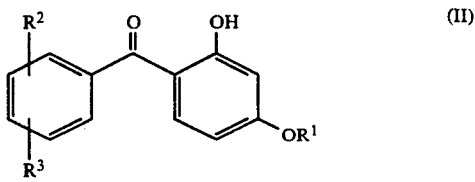

with chlorosulfonic acid at from −20° to +100° C. and under a pressure of from 0.01 to 50 bar in a solvent selected from the group consisting of aliphatic, cycloaliphatic and aromatic carboxylates and mixtures thereof.

2. A process as claimed in claim 1, wherein the process is carried out at from 0° to 40° C. and under a pressure of from 0.1 to 2 bar.

3. A process as claimed in claim 1, wherein a mixture of carboxylates is used as the solvent.

4. A process as claimed in claim 1, wherein the carboxylate is ethyl acetate.

5. A process as claimed in claim 1, wherein the carboxylate is ethyl benzoate.

6. A process as claimed in claim 1, wherein the carboxylate is dimethyl phthalate.

* * * * *